United States Patent
Choe et al.

(10) Patent No.: US 11,214,665 B2
(45) Date of Patent: Jan. 4, 2022

(54) POLYMERIZATION INITIATOR COMPOSITION, PREPARATION METHOD THEREFOR, AND METHOD FOR PREPARING POLYMER USING SAME

(71) Applicant: LG Chem, Ltd., Seoul (KR)

(72) Inventors: Jae Hoon Choe, Daejeon (KR); Jong Young Choi, Daejeon (KR); Dong Cheol Choe, Daejeon (KR); Hyun Ju Kim, Daejeon (KR); Hyeon Hui Kim, Daejeon (KR); Jung Yong Lee, Daejeon (KR); Chan Joong Kim, Daejeon (KR); Myung Han Lee, Daejeon (KR); Hye Jin Han, Daejeon (KR)

(73) Assignee: LG Chem, Ltd.

( * ) Notice: Subject to any disclaimer, the term of this patent is extended or adjusted under 35 U.S.C. 154(b) by 302 days.

(21) Appl. No.: 16/468,998

(22) PCT Filed: Dec. 27, 2017

(86) PCT No.: PCT/KR2017/015531
§ 371 (c)(1),
(2) Date: Jun. 12, 2019

(87) PCT Pub. No.: WO2018/128315
PCT Pub. Date: Jul. 12, 2018

(65) Prior Publication Data
US 2019/0330447 A1    Oct. 31, 2019

(30) Foreign Application Priority Data

Jan. 4, 2017  (KR) .................. 10-2017-0001272

(51) Int. Cl.
*C08K 5/18*     (2006.01)
*C07C 209/70*   (2006.01)
(Continued)

(52) U.S. Cl.
CPC .............. *C08K 5/18* (2013.01); *C07C 209/70* (2013.01); *C07C 211/53* (2013.01); *C08F 236/10* (2013.01)

(58) Field of Classification Search
CPC ....... C08K 5/18; C07C 209/70; C07C 211/53; C08F 236/10
(Continued)

(56) References Cited

U.S. PATENT DOCUMENTS 5,112,920 A    5/1992 Haag
5,554,696 A *  9/1996 Fayt .......................... C08F 4/48
                                          260/665 R
(Continued)

FOREIGN PATENT DOCUMENTS

CN    1777641 A    5/2006
CN    103848941 A  6/2014
(Continued)

OTHER PUBLICATIONS

Kleij AW, Kleijn H, Jastrzebski JT, Smeets WJ, Spek AL, van Koten G. Dendritic Carbosilanes Containing Silicon-Bonded 1-[C6H2 (CH2NMe2) 2-3, 5-Li-4] or 1-[C6H3 (CH2NMe2)-4-Li-3] Mono- and Bis (amino) aryllithium End Groups: Structure of {[CH2SiMe2C6H3 (CH2NMe2)-4-Li-3] 2} 2. Organometallics. Jan. 18, 1999;18(2):268-76.
(Continued)

*Primary Examiner* — Michael M. Bernshteyn
(74) *Attorney, Agent, or Firm* — Lerner, David, Littenberg, Krumholz & Mentlik, LLP

(57) ABSTRACT

A polymerization initiator composition includes isomers of the polymerization initiator, thereby preventing instability and inertness of the polymerization initiator and physical property degradation of the SSBR, minimizing by-products and unreacted materials, and remarkably improving a con-
(Continued)

version ratio. In addition, when the polymerization initiator composition according to the present invention is used, there is no need to add a polar additive separately upon polymer polymerization, since the polar additive is already added at the time of preparing the polymerization initiator. Further, the polymer initiator composition has high polarity so that the hydrophobic SSBR and the hydrophilic silica can be effectively dispersed.

12 Claims, 5 Drawing Sheets

(51) Int. Cl.
*C07C 211/53* (2006.01)
*C08F 236/10* (2006.01)

(58) Field of Classification Search
USPC .......................................................... 526/180
See application file for complete search history.

(56) References Cited

U.S. PATENT DOCUMENTS

| | | | |
|---|---|---|---|
| 5,567,815 A * | 10/1996 | Hall | C07F 1/02 |
| | | | 502/157 |
| 5,744,511 A | 4/1998 | Kazama et al. | |
| 6,339,116 B1 | 1/2002 | Afzali-Ardakani et al. | |
| 9,200,135 B2 * | 12/2015 | Lee | C08F 2/00 |
| 9,309,371 B2 * | 4/2016 | Lee | C08F 236/10 |
| 2003/0216515 A1 | 11/2003 | Swarup et al. | |
| 2006/0036050 A1 * | 2/2006 | Antkowiak | C08F 36/04 |
| | | | 526/175 |
| 2006/0217470 A1 | 9/2006 | Mikami et al. | |
| 2007/0123631 A1 | 5/2007 | Halasa et al. | |
| 2012/0101212 A1 * | 4/2012 | Yoon | C07F 7/1804 |
| | | | 524/534 |
| 2014/0163163 A1 * | 6/2014 | Lee | C07D 213/16 |
| | | | 524/575 |
| 2014/0213714 A1 | 7/2014 | Ono et al. | |
| 2015/0175773 A1 | 6/2015 | Lee et al. | |
| 2016/0159956 A1 * | 6/2016 | Thiele | C08F 236/10 |
| | | | 524/526 |
| 2017/0015763 A1 | 1/2017 | Joe et al. | |

FOREIGN PATENT DOCUMENTS

| | | |
|---|---|---|
| CN | 103958590 A | 7/2014 |
| EP | 3103820 A1 | 12/2016 |
| KR | 100228945 B1 | 11/1999 |
| KR | 100290438 A | 7/2000 |
| KR | 20150003120 A | 1/2015 |
| KR | 20160075127 A | 6/2016 |

OTHER PUBLICATIONS

International Search Report for PCT/KR2017/015531 dated Oct. 5, 2018.
Extended European Search Report with Written Opinion for Application No. EP 17889595.9 dated Nov. 5, 2019, 3 pages.
Kazunori, et al., "Anionic Polymerization of Tertiary Aminostyrenes and Characterization of the Polymers," Polymer Journal, Feb. 10, 1988, pp. 791-799, vol. 20, No. 9.
Search Report from Chinese Office Action for Application No. 2017800768785 dated Jul. 2, 2020; 3 pages.
Zhang X, Yu X, Yao J, Jiang M. Synthesis and nonlinear optical properties of two three-branched two-photon polymerization initiators. Synthetic Metals. Dec. 1, 2008;158(21-24):964-8. Abstract Only. <https://www.sciencedirect.com/journal/synthetic-metals/vol/158/issue/21>.

* cited by examiner

[Figure 1]
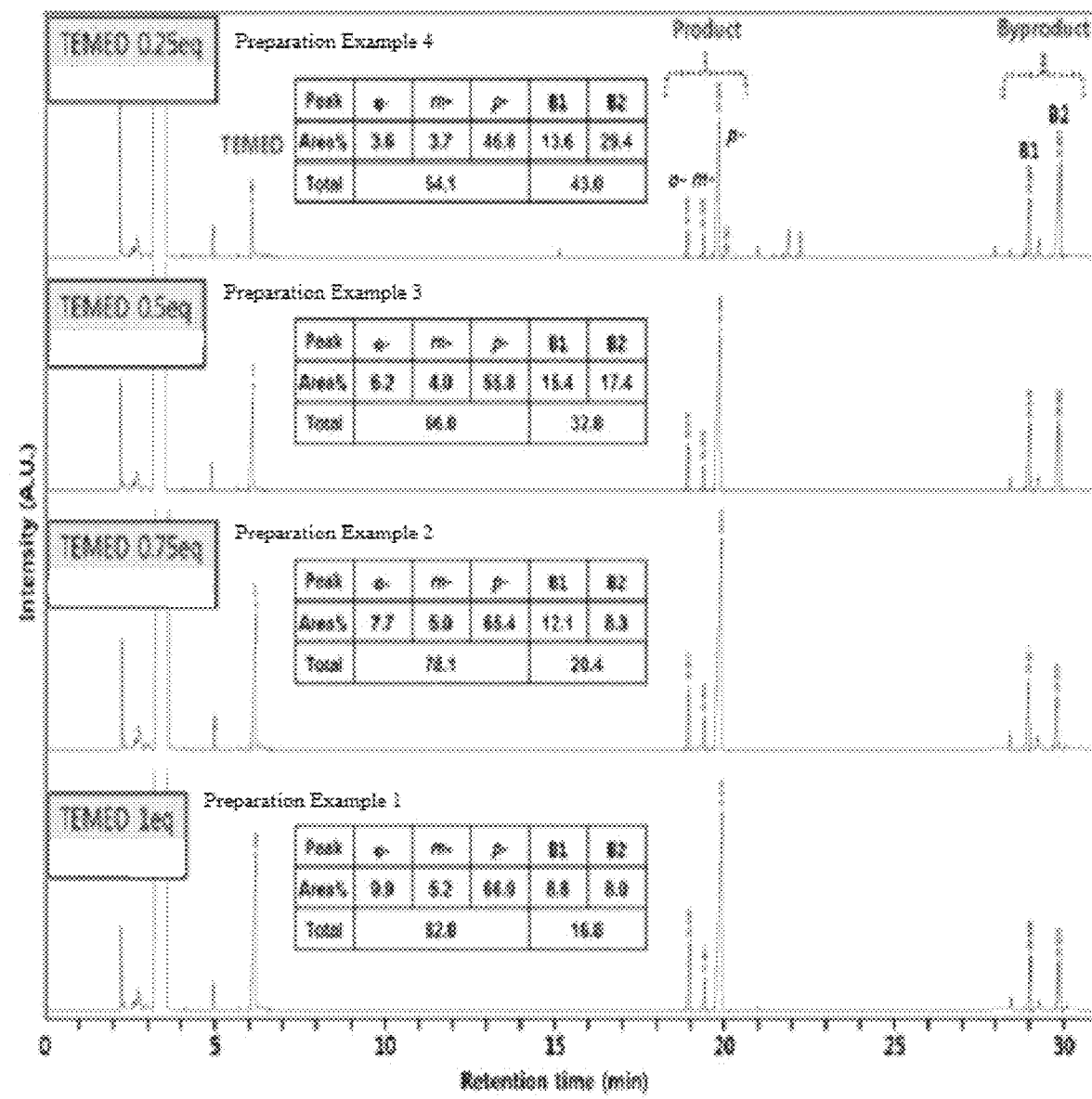

[Figure 2]
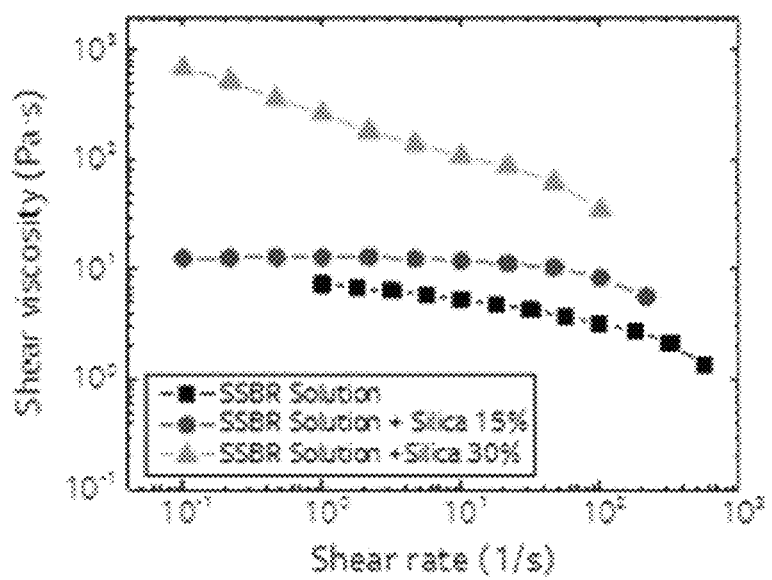
[Figure 3]
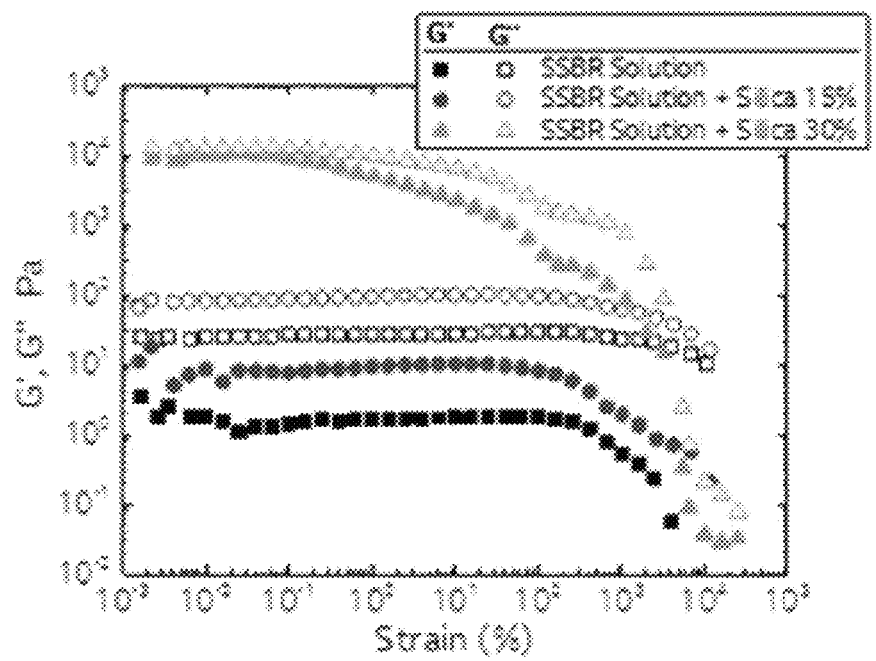

[Figure 4]
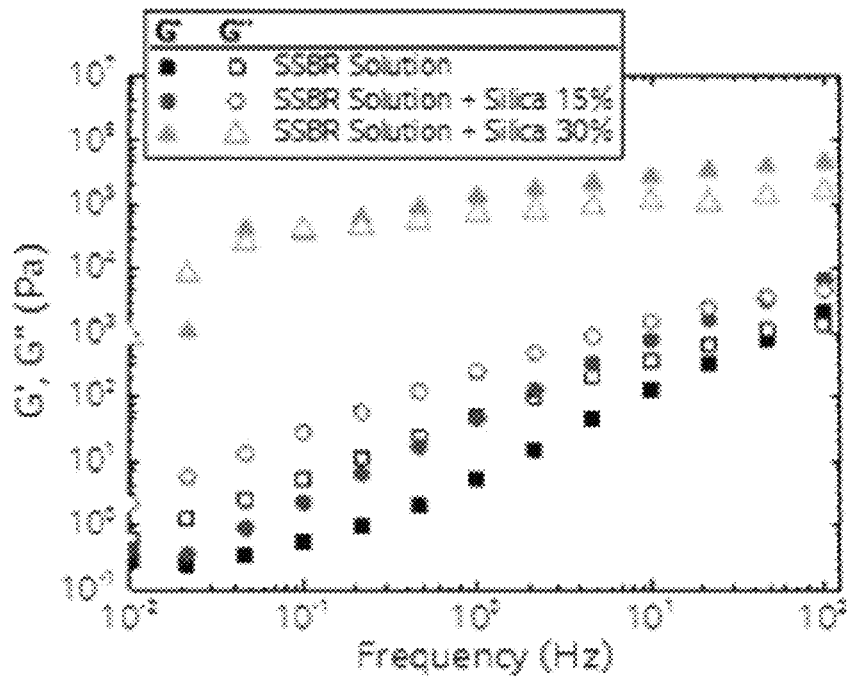
[Figure 5]
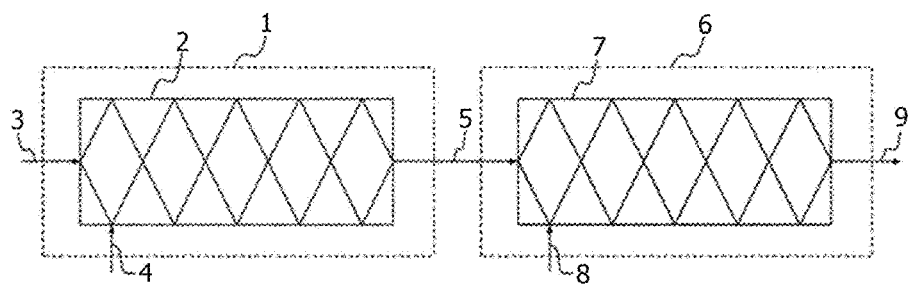
[Figure 6]
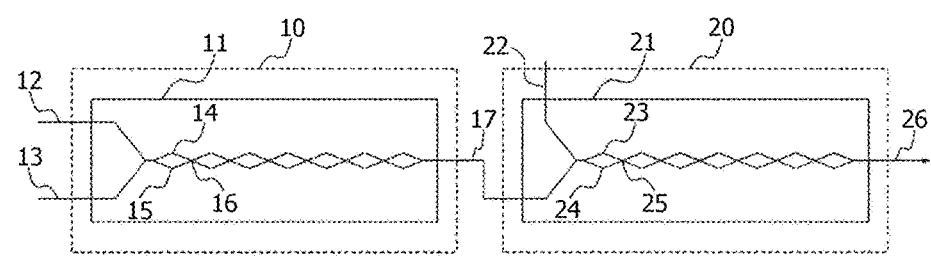

[Figure 7]
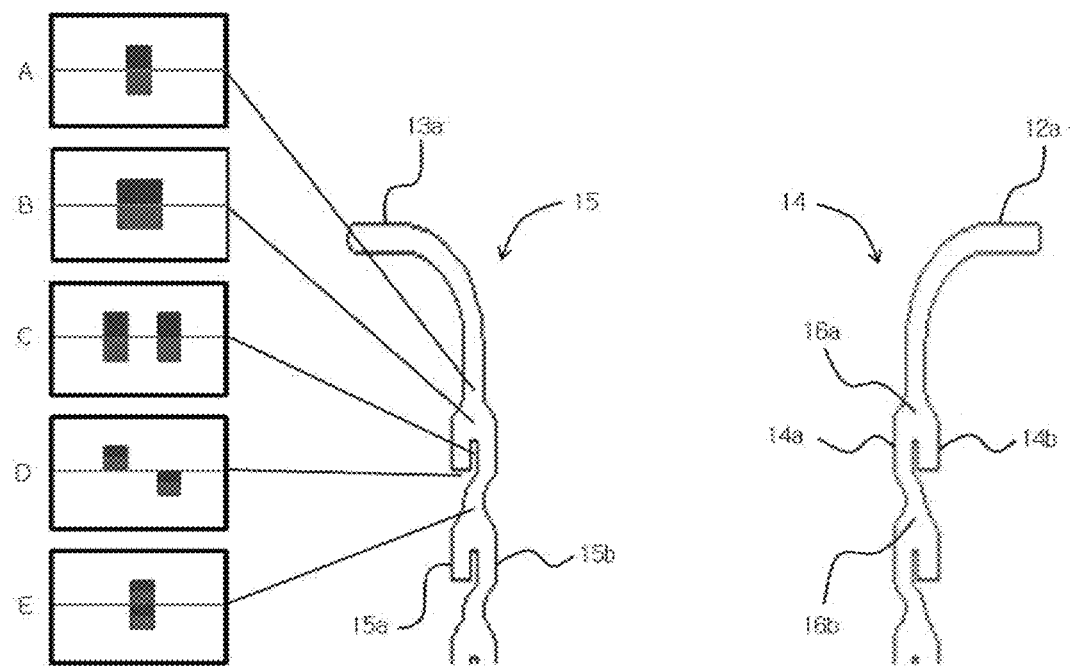

[Figure 8]
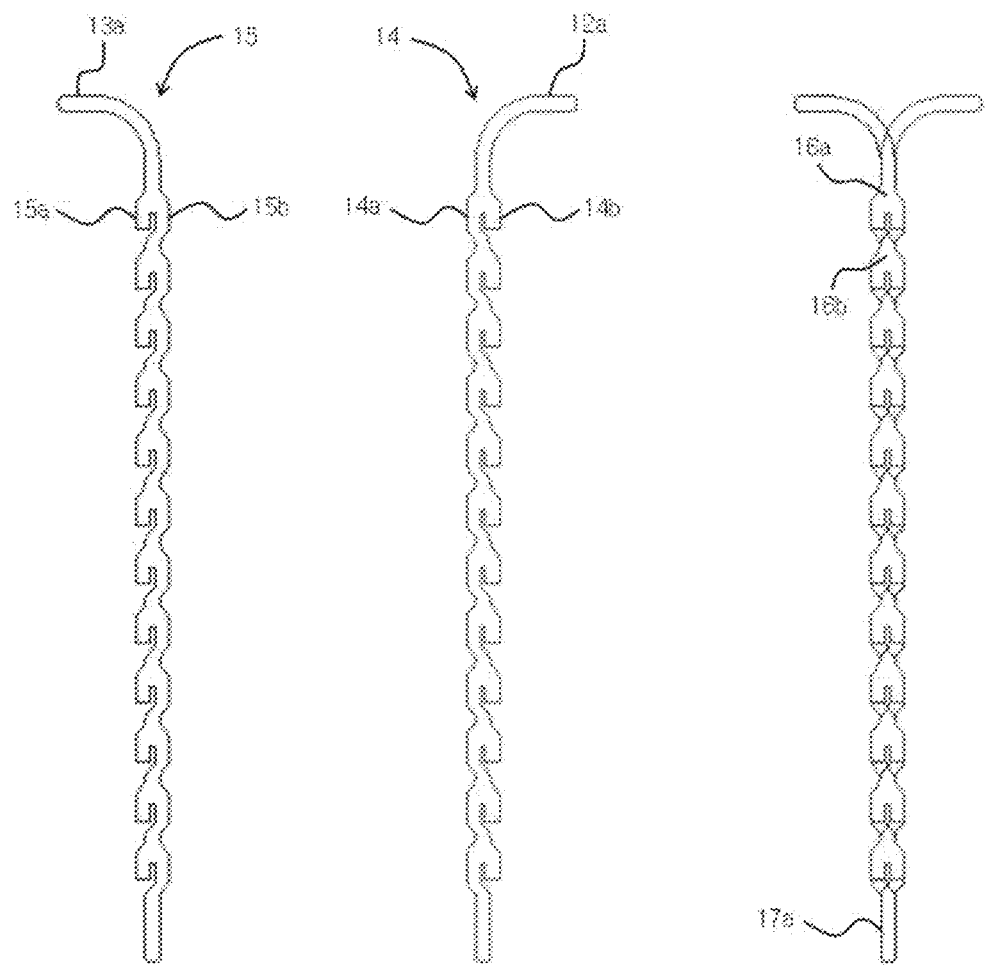
[Figure 9]
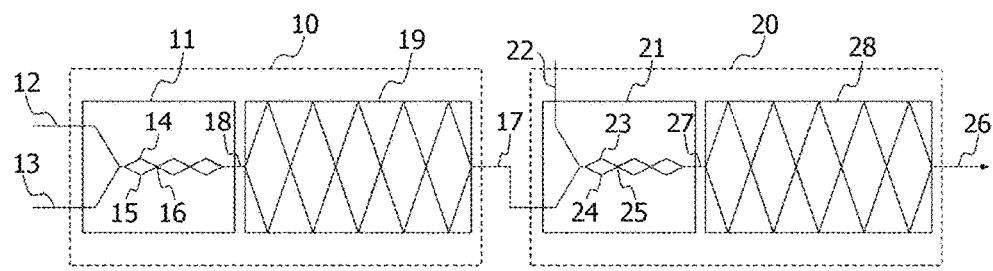

POLYMERIZATION INITIATOR COMPOSITION, PREPARATION METHOD THEREFOR, AND METHOD FOR PREPARING POLYMER USING SAME

CROSS-REFERENCE TO RELATED APPLICATIONS

This application is a national phase entry under U.S.C. § 371 of International. Application No. PCT/KR2017/015531, filed Dec. 27, 2017, which claims priority to Korean Patent Application No. 10-2017-0001272, filed Jan. 4, 2017, the disclosures of which are incorporated herein by reference.

TECHNICAL FIELD

The present invention relates to a polymerization initiator composition, a preparation method thereof, and a method for preparing a polymer using the same.

BACKGROUND ART

As highly efficient, eco-friendly and high-performance tire properties are required for carbon dioxide emission reduction, fuel efficiency improvement and the like, tire materials that meet such needs are being actively developed. In particular, unlike emulsion polymerization, a styrene-butadiene polymer obtained by solution polymerization (hereinafter referred to as SSBR (Solution Styrene Butadiene Rubber)) has been used as a rubber material for tire treads by being easy to change in structure, and reducing movement of chain ends and increasing bonding force with carbon black due to bonding or modification of chain ends. In addition, as silica filling materials are developed, a low rolling resistance value and high road surface braking force can be obtained at the same time, but to this end, a technique in which hydrophilic silica must be combined with the hydrophobic SSBR and dispersed therein is needed.

Such a method includes a method of covering the silica particles themselves with a hydrophobic substance, a method of using a coupling agent between silica and SSBR, and the like. In recent years, techniques for introducing a moiety capable of reacting and bonding with silica or a moiety serving to assist the reaction and bonding into the SSBR polymer chain itself have been developed by using a modified initiator, a modified monomer or a modifying agent, and the like upon SSBR anionic polymerization. In particular, the modified initiator initiates anionic polymerization and simultaneously serves to introduce a functional group at one end of the chain, thereby being used as an essential material for producing such modified SSBR.

A hexamethyleneimine lithium (HMI-Li) initiator among the anionic polymerization initiators used in the synthesis of this SSBR is prepared by reacting hexamethyleneimine (HMI) with n-butyllithium (BuLi, NBL) as shown in the following Reaction Scheme 1.

[Reaction Scheme 1]

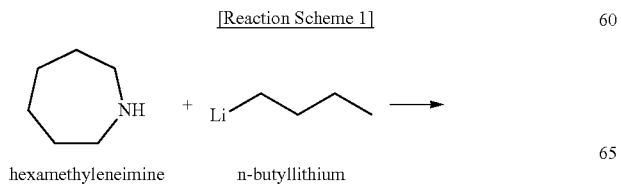

hexamethyleneimine    n-butyllithium

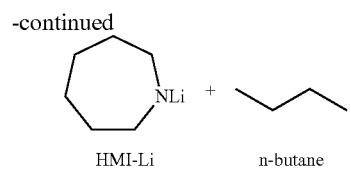

HMI-Li    n-butane

However, since HMI-Li has low solubility in solvents, it falls into precipitation over time, and although it can also be used as an initiator, it has a problem in that it is less reactive than BuLi. In order to solve these drawbacks, conventionally, after Reaction Scheme 1, a conjugated diene (R) such as isoprene (IP) or 1,3-butadiene (BD) was further reacted to prepare a polymerization initiator, as shown in the following Reaction Scheme 2. Due to the addition of such a conjugated diene, the solubility in an organic solvent can increase to achieve a stable reaction, and the reactivity as an initiator also becomes higher than that of HMI-Li, thereby being sufficient to initiate polymerization.

[Reaction Scheme 2]

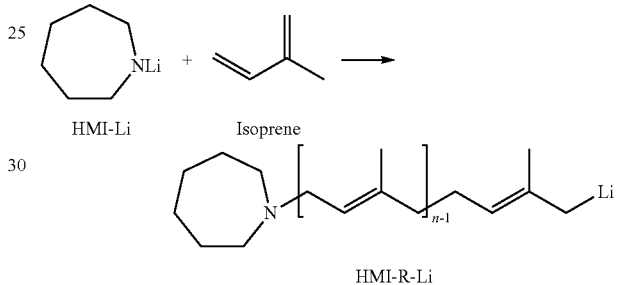

In Reaction Scheme 2, n is an integer from 1 to 100.

However, the modified initiator thus prepared has a problem that a polar additive should be further introduced upon the SSBR polymerization.

DISCLOSURE

Technical Problem

The present invention has been made to solve the above-described problems, and it is an object of the present invention to provide a polymerization initiator composition comprising an isomer of a polymerization initiator and containing a polar substituent group, a preparation method thereof, and a method for preparing a polymer using the same.

Technical Solution

In order to achieve the above-mentioned object,
the present invention provides a polymerization initiator composition comprising a compound represented by Formula 1 below:

[Formula 1]

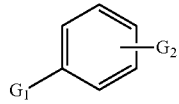

In Formula 1 above, $G_1$ and $G_2$ include two or more of ortho, meta and para isomers based on the benzene structure disclosed in Formula 1, but include the case where $G_1$ and $G_2$ are a para isomer, where $G_1$ is a substituent group containing an alkali metal or an alkali earth metal, $G_1$ is a form in which alkyl lithium having 1 to 20 carbon atoms, alkyl sodium having 1 to 20 carbon atoms, alkyl potassium having 1 to 20 carbon atoms, alkyl magnesium bromide having 1 to 6 carbon atoms or alkyl magnesium chloride having 1 to 6 carbon atoms is substituted for the benzene structure disclosed in Formula 1, a polar substituent group forms a coordination bond on the basis of the alkali metal or alkali earth metal contained in $G_1$, and $G_2$ is represented by Formula 1-a below,

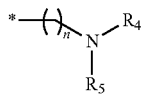

[Formula 1-a]

in Formula 1-a above, $R_4$ and $R_5$ independently represent hydrogen or an alkyl group having 1 to 5 carbon atoms, n is an integer of 0 to 20, the case where n is 0 represents a single bond, and in the benzene structure of Formula 1, the carbons to which $G_1$ and $G_2$ are not bonded are independently bonded by hydrogen or an alkyl group having 1 to 6 carbon atoms.

Furthermore, the present invention provides a method for preparing a polymerization initiator composition comprising steps of: reacting a compound represented by Formula 2 below; and an organometallic compound to prepare a modified initiator; and reacting the modified initiator as prepared and a polar additive:

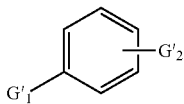

[Formula 2]

In Formula 2 above, $G'_1$ and $G'_2$ include two or more of ortho, meta and para isomers based on the benzene structure disclosed in Formula 2, but include the case where $G'_1$ and $G'_2$ are a para isomer, where $G'_1$ is represented by Formula 2-a below and $G'_2$ is represented by Formula 2-b below,

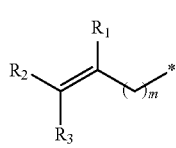

[Formula 2-a]

in Formula 2-a above, $R_1$, $R_2$ and $R_3$ independently represent hydrogen, an alkyl group having 1 to 6 carbon atoms, an alkenyl group having 1 to 6 carbon atoms or an alkynyl group having 1 to 6 carbon atoms, m is an integer of 0 to 20, and the case where m is 0 represents a single bond, and

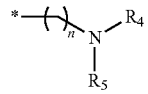

[Formula 2-b]

in Formula 2-b below, $R_4$ and $R_5$ independently represent hydrogen or an alkyl group having 1 to 5 carbon atoms, n is an integer of 0 to 20, the case where n is 0 represents a single bond, and in the benzene structure of Formula 2, the carbons to which $G'_1$ and $G'_2$ are not bonded are independently bonded by hydrogen or an alkyl group having 1 to 6 carbon atoms.

Moreover, the present invention provides a method for preparing a polymer comprising a step of reacting a polymerization initiator composition comprising a compound represented by Formula 1 below; a resin monomer; and a conjugated diene compound:

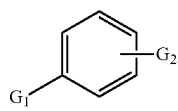

[Formula 1]

In Formula 1 above, $G_1$ and $G_2$ include two or more of ortho, meta and para isomers based on the benzene structure disclosed in Formula 1, but include the case where $G_1$ and $G_2$ are a para isomer, where $G_1$ is a substituent group containing an alkali metal or an alkali earth metal, $G_1$ is a form in which alkyl lithium having 1 to 20 carbon atoms, alkyl sodium having 1 to 20 carbon atoms, alkyl potassium having 1 to 20 carbon atoms, alkyl magnesium bromide having 1 to 6 carbon atoms or alkyl magnesium chloride having 1 to 6 carbon atoms is substituted for the benzene structure disclosed in Formula 1, a polar substituent group forms a coordination bond on the basis of the alkali metal or alkali earth metal contained in $G_1$, and $G_2$ is represented by Formula 1-a below,

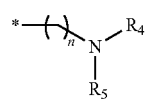

[Formula 1-a]

in Formula 1-a above, $R_4$ and $R_5$ independently represent hydrogen or an alkyl group having 1 to 5 carbon atoms, n is an integer of 0 to 20, the case where n is 0 represents a single bond, in the benzene structure of Formula 1, the carbons to which $G_1$ and $G_2$ are not bonded are independently bonded by hydrogen or an alkyl group having 1 to 6 carbon atoms.

Advantageous Effects

The polymerization initiator composition according to the present invention can comprise isomers of the polymerization initiator, thereby preventing instability and inertness of the polymerization initiator and physical property degradation of the SSBR, minimizing by-products and unreacted materials, and remarkably improving a conversion ratio.

In addition, the polymerization initiator composition according to the present invention does not need to add a polar additive separately upon polymer polymerization, since the polar additive is already added at the time of preparing the polymerization initiator, and there is an advantage of effectively dispersing the hydrophobic SSBR and the hydrophilic silica.

BRIEF DESCRIPTION OF DRAWINGS

FIG. 1 is a graph of gas chromatography (GC) of polymerization initiator compositions according to the present invention.

FIG. 2 is a graph of shear viscosity versus shear rate of polymerization initiator compositions according to the present invention.

FIG. 3 is a graph of storage elastic modulus and loss elastic modulus versus pressure (strain) of polymerization initiator compositions according to the present invention.

FIG. 4 is a graph of storage elastic modulus and loss modulus versus frequency of polymerization initiator compositions according to the present invention.

FIG. 5 is a schematic configuration diagram of a polymerization initiator production apparatus according to one embodiment of the present invention.

FIG. 6 is a schematic configuration diagram of a polymerization initiator production apparatus according to another embodiment of the present invention.

FIG. 7 shows a detailed structure of microchannels according to another embodiment of the present invention and a fluid flow in the microchannels.

FIG. 8 shows a separation structure and a combination structure of a lower microchannel and an upper microchannel according to another embodiment of the present invention.

FIG. 9 is a schematic configuration diagram of a polymerization initiator production apparatus according to another embodiment of the present invention.

BEST MODE

Hereinafter, the present invention will be described in detail. The following detailed description is intended to illustrate the embodiments of the present invention in detail, and thus, even if there are definite expressions, the right scope defined by the claims is not limited.

The present invention provides a polymerization initiator composition comprising a compound represented by Formula 1 below:

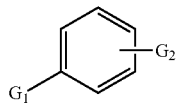

[Formula 1]

In Formula 1 above, $G_1$ and $G_2$ include two or more of ortho, meta and para isomers based on the benzene structure disclosed in Formula 1, but include the case where $G_1$ and $G_2$ are a para isomer, where $G_1$ is a substituent group containing an alkali metal or an alkali earth metal, $G_1$ is a form in which alkyl lithium having 1 to 20 carbon atoms, alkyl sodium having 1 to 20 carbon atoms, alkyl potassium having 1 to 20 carbon atoms, alkyl magnesium bromide having 1 to 6 carbon atoms or alkyl magnesium chloride having 1 to 6 carbon atoms is substituted for the benzene structure disclosed in Formula 1, a polar substituent group forms a coordination bond on the basis of the alkali metal or alkali earth metal contained in $G_1$, and $G_2$ is represented by Formula 1-a below,

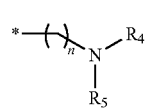

[Formula 1-a]

in Formula 1-a above, $R_4$ and $R_5$ independently represent hydrogen or an alkyl group having 1 to 5 carbon atoms, n is an integer of 0 to 20, the case where n is 0 represents a single bond, and in the benzene structure of Formula 1, the carbons to which $G_1$ and $G_2$ are not bonded are independently bonded by hydrogen or an alkyl group having 1 to 6 carbon atoms.

In the present invention, the "alkyl group" is defined as a functional group derived from a linear or branched saturated hydrocarbon.

A specific example of the alkyl group may include a methyl group, an ethyl group, an n-propyl group, an isopropyl group, an n-butyl group, a sec-butyl group, a tert-butyl group, an n-pentyl group, an 1,1-dimethylpropyl group, an 1,2-dimethylpropyl group, a 2,2-dimethylpropyl group, an 1-ethylpropyl group, a 2-ethylpropyl group, an n-hexyl group, an 1-methyl-2-ethylpropyl group, an 1-ethyl-2-methylpropyl group, an 1,1,2-trimethylpropyl group, an 1-propylproypl group, an 1-methylbutyl group, a 2-methylbutyl group, an 1,1-dimethylbutyl group, an 1,2-dimethylbutyl group, a 2,2-dimethylbutyl group, an 1,3-dimethylbutyl group, a 2,3-dimethylbutyl group, a 2-ethylbutyl group, a 2-methylpentyl group or a 3-methylpentyl group, and the like.

In the present invention, the "alkenyl group" or "alkynyl group" means that at least one carbon-carbon double bond or triple bond is contained in the middle or end of the alkyl group as defined above.

By comprising the compound represented by Formula 1 as above, the polymerization initiator composition of the present invention has high polarity, so that hydrophobic SSBR and hydrophilic silica can be effectively dispersed.

In one example, the compound represented by Formula 1 may have a ratio of the sum weight of the ortho and meta isomers to the weight of the para isomer in a range of 1 to 4:6 to 9. Specifically, the ratio of the sum weight of the ortho and meta isomers and the weight of the para isomer may be in a range of 2 to 3:7 to 9. By having the weight ratio of isomers in the above range, the stability of the polymerization initiator composition can be improved.

In one example, the polar substituent group may have a structure in which one or more of tetrahydrofuran, ditetrahydrofurylpropane, diethyl ether, cycloamyl ether, dipropyl ether, ethylenedimethyl ether, ethylenedimethyl ether, diethylene glycol, dimethyl ether, tert-butoxyethoxyethane, bis(2-dimethylaminoethyl) ether, (dimethylaminoethyl)ethyl ether, dioxane, ethylene glycol dimethyl ether, ethylene glycol dibutyl ether, diethylene glycol dimethyl ether, diethylene glycol dibutyl ether, dimethoxybenzene, 2,2-bis(2-oxolanyl)propane, dipiperidinoethane, pyridine, quinuclidine, trimethylamine, triethylamine, tripropylamine, tetramethylethylenediamine, potassium tert-butyrate, sodium tert-butyrate, sodium amylate and triphenylphosphine are coordination-bonded to an alkali metal or an alkali earth metal contained in G1. Specifically, the polar substituent may have a structure in which one or more of tetrahydrofuran and tetramethylethylenediamine are coordination-bonded to an alkali metal or an alkali earth metal contained in G1.

In one example, the polymerization initiator according to the present invention may comprise compounds represented by Formulas 3 to 5 below:

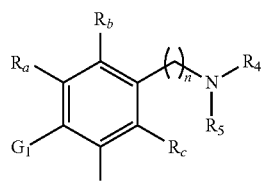

[Formula 3]

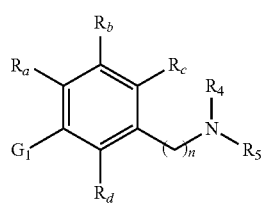

[Formula 4]

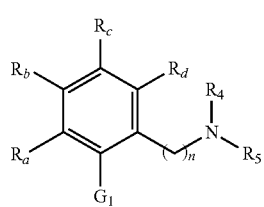

[Formula 5]

In Formulas 3 to 5 above, $G_1$ is a substituent group containing an alkali metal or an alkali earth metal, where $G_1$ is a form in which alkyl lithium having 1 to 20 carbon atoms, alkyl sodium having 1 to 20 carbon atoms, alkyl potassium having 1 to 20 carbon atoms, alkyl magnesium bromide having 1 to 6 carbon atoms or alkyl magnesium chloride having 1 to 6 carbon atoms is substituted for the benzene structure disclosed in Formulas 3 to 5, a polar substituent group forms a coordination bond on the basis of the alkali metal or alkali earth metal contained in $G_1$, $R_1$, $R_2$ and $R_3$ independently represent hydrogen or an alkyl group having 1 to 5 carbon atoms, an alkenyl group having 1 to 6 carbon atoms or an alkynyl group having 1 to 6 carbon atoms, $R_4$ and $R_5$ independently represent hydrogen or an alkyl group having 1 to 5 carbon atoms, $R_a$, $R_b$, $R_c$, and $R_d$ independently represent hydrogen or an alkyl group having 1 to 6 carbon atoms, n is an integer of 0 to 20, and the case where n is 0 represents a single bond.

For example, in Formulas 3 to 5, n may be an integer of 0 to 15, an integer of 0 to 10, or an integer of 0 to 5.

Specifically, the polymerization initiator composition according to the present invention may comprise compounds represented by Formulas 6 to 8 below:

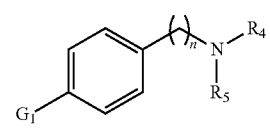

[Formula 6]

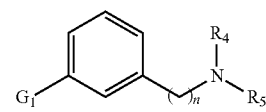

[Formula 7]

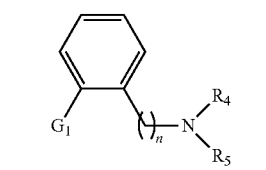

[Formula 8]

In Formulas 6 to 8 above, $G_1$ is a substituent group containing an alkali metal or an alkali earth metal, where $G_1$ is a form in which alkyl lithium having 1 to 20 carbon atoms, alkyl sodium having 1 to 20 carbon atoms, alkyl potassium having 1 to 20 carbon atoms, alkyl magnesium bromide having 1 to 6 carbon atoms or alkyl magnesium chloride having 1 to 6 carbon atoms is substituted for the benzene structure disclosed in Formulas 6 to 8, a polar substituent group forms a coordination bond on the basis of the alkali metal or alkali earth metal contained in $G_1$, $R_4$ and $R_5$ independently represent hydrogen or an alkyl group having 1 to 5 carbon atoms, n is an integer of 0 to 20, and the case where n is 0 represents a single bond.

For example, in Formulas 6 to 8, n may be an integer of 0 to 15, an integer of 0 to 10, or an integer of 0 to 5.

Furthermore, the present invention, provides a method for preparing a polymerization initiator composition comprising steps of: reacting a compound represented by Formula 2; and an organometallic compound to prepare a modified initiator; and reacting the modified initiator as prepared and a polar additive:

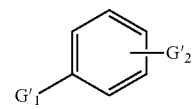

[Formula 2]

In Formula 2 above,

G'₁ and G'₂ include two or more of ortho, meta and para isomers based on the benzene structure disclosed in Formula 2, but include the case where G'₁ and G'₂ are a para isomer, where G'₁ is represented by Formula 2-a below and G'₂ is represented by Formula 2-b below,

[Formula 2-a]

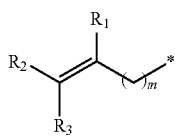

in Formula 2-a above, $R_1$, $R_2$ and $R_3$ independently represent hydrogen, an alkyl group having 1 to 6 carbon atoms, an alkenyl group having 1 to 6 carbon atoms or an alkynyl group having 1 to 6 carbon atoms, m is an integer of 0 to 20, and the case where m is 0 represents a single bond, and

[Formula 2-b]

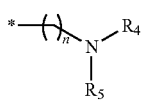

in Formula 2-b below, $R_4$ and $R_5$ independently represent hydrogen or an alkyl group having 1 to 5 carbon atoms, n is an integer of 0 to 20, the case where n is 0 represents a single bond, and in the benzene structure of Formula 2, the carbons to which G'₁ and G'₂ are not bonded are independently bonded by hydrogen or an alkyl group having 1 to 6 carbon atoms.

Specifically, the compound represented by Formula 2; and the polar additive may be reacted first and the organometallic compound may be reacted.

In one example, the compound represented by Formula 2 may have a ratio of the sum weight of the ortho and meta isomers to the weight of the para isomers in a range of 1 to 4:6 to 9. Specifically, the ratio of the sum weight of the ortho and meta isomers to the weight of the para isomer may be in a range of 2 to 3:7 to 9. By having the weight ratio of isomers in the above range, the stability of the polymerization initiator composition is improved, whereby the yield of the polymer can be excellent.

In one example, the compound represented by Formula 2 may comprise Formulas 9 to 11 below:

[Formula 9]

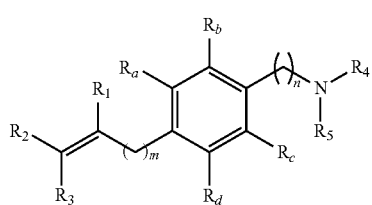

[Formula 10]

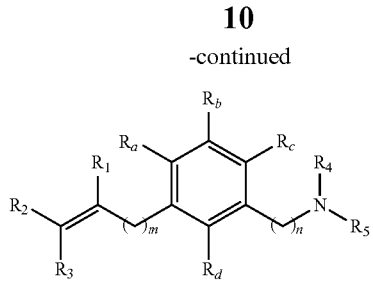

[Formula 11]

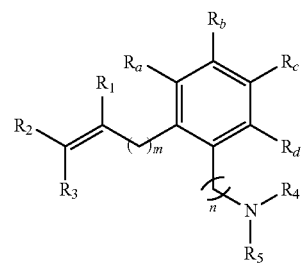

In Formulas 9 to 11 above, $R_1$, $R_2$ and $R_3$ independently represent hydrogen or an alkyl group having 1 to 5 carbon atoms, an alkenyl group having 1 to 6 carbon atoms or an alkynyl group having 1 to 6 carbon atoms, $R_4$ and $R_5$ independently represent hydrogen or an alkyl group having 1 to 5 carbon atoms, $R_a$, $R_b$, $R_c$, and $R_d$ independently represent hydrogen or an alkyl group having 1 to 6 carbon atoms, m and n are independently an integer of 0 to 20, and the case where morn is 0 represents a single bond.

For example, in Formulas 9 to 11, m and n may independently be an integer of 0 to 15, an integer of 0 to 10, or an integer of 0 to 5.

Specifically, the compound represented by Formula 2 above may comprise compounds represented by Formulas 12 to 14:

[Formula 12]

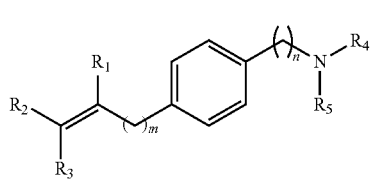

[Formula 13]

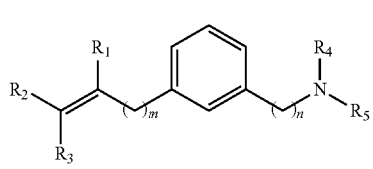

[Formula 14]

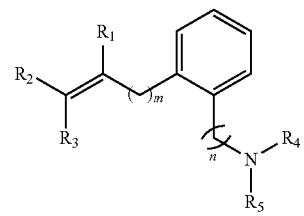

In Formulas 12 to 14 above, $R_1$, $R_2$ and $R_3$ independently represent hydrogen, an alkyl group having 1 to 6 carbon atoms, an alkenyl group having 1 to 6 carbon atoms or an alkynyl group having 1 to 6 carbon atoms, $R_4$ and $R_5$ independently represent hydrogen or an alkyl group having 1 to 5 carbon atoms, m and n are independently an integer of 0 to 20, and the case where m or n is 0 represents a single bond.

For example, in Formulas 12 to 14, m and n may independently be an integer of 0 to 15, an integer of 0 to 10, or an integer of 0 to 5.

More specifically, the compound represented by Formula 2 above may comprise compounds represented by Formulas 15 to 17 below:

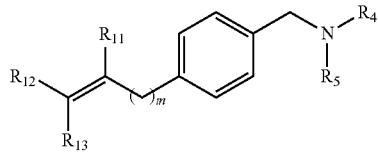
[Formula 15]

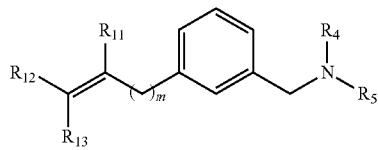
[Formula 16]

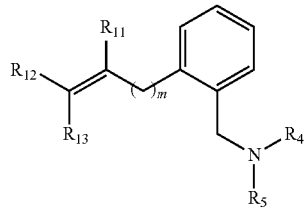
[Formula 17]

In Formulas 15 to 17 above, $R_{11}$, $R_{12}$ and $R_{13}$ independently represent hydrogen or an alkyl group having 1 to 6 carbon atoms, $R_4$ and $R_5$ independently represent hydrogen or an alkyl group having 1 to 5 carbon atoms, m is an integer of 0 to 20, and the case where m is 0 represents a single bond.

For example, in Formulas 15 to 17, m and n may independently be an integer of 0 to 15, an integer of 0 to 10, or an integer of 0 to 5.

In addition, the compound represented by Formula 2 below may comprise compounds of Formulas 18 to 20 below:

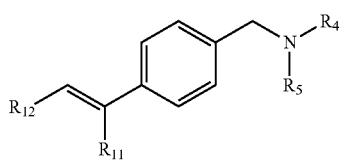
[Formula 18]

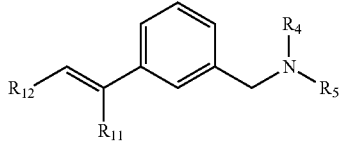
[Formula 19]

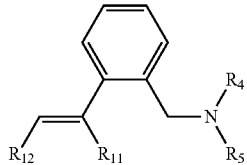
[Formula 20]

In Formulas 18 to 20 above, $R_{11}$, $R_{12}$ and $R_{13}$ independently represent hydrogen or an alkyl group having 1 to 6 carbon atoms, and $R_4$ and $R_5$ independently represent hydrogen or an alkyl group having 1 to 5 carbon atoms.

For example, the compound represented by Formula 2 may be 2-vinyl-N,N-dimethylbenzylamine, 3-vinyl-N,N-dimethylbenzylamine, 4-vinyl-N,N-dimethylbenzylamine, N,N-diethyl-2-vinylaniline, N,N-diethyl-3-vinylaniline, N,N-diethyl-4-vinylaniline, N,N-dimethyl-2-(2-vinylphenyl)ethane-1-amine, N,N-dimethyl-2-(3-vinylphenyl)ethane-1-amine, N,N-dimethyl-2-(4-vinylphenyl)ethane-1-amine, N,N-diethyl-2-(2-vinylphenyl)ethanamine, N,N-diethyl-2-(3-vinylphenyl)ethanamine or N,N-diethyl-2-(4-vinylphenyl)ethanamine. Specifically, the compound represented by Formula 2 may be 2-vinyl-N,N-dimethylbenzylamine, 3-vinyl-N,N-dimethylbenzylamine, 4-vinyl-N,N-dimethylbenzylamine, N,N-diethyl-2-vinylaniline, N,N-diethyl-3-vinylaniline or N,N-diethyl-4-vinylaniline.

In one example, in the step of preparing the modified initiator, the organometallic compound may comprise an organic component and a metal component, and optionally, may further comprise a Br (bromine) element or a chlorine (Cl) element. Here, the organic component may be composed of an alkyl group having 1 to 10 carbon atoms, an aryl group having 1 to 10 carbon atoms, an alkenyl group having 1 to 10 carbon atoms, and the like. Specifically, the organic component may be an n-butyl group, an n-pentyl group, an s-butyl group or a t-butyl group, and more specifically, may be an n-butyl group. Furthermore, the metal component may be an alkali metal or an alkali earth metal. Specifically, it may be lithium, sodium, potassium, magnesium, rubidium, cesium, strontium, beryllium or calcium, and more specifically, may be lithium.

For example, the organometallic compound may comprise one or more selected from the group consisting of an organic alkali metal compound and an organic alkali earth metal compound. Specifically, as the alkali metal compound, one or more selected from the group consisting of alkyl lithium, aryl lithium, alkenyl lithium, alkyl sodium, aryl sodium, alkenyl sodium, alkyl potassium, alkenyl potassium and aryl potassium may be used, and more specifically, n-butyl lithium (NBL) may be used. Furthermore, the alkali earth metal compound may be an organomagnesium compound, an organocalcium compound or an organostrontium compound, containing a Br (bromine) element or a chlorine (Cl) element, and more specifically, alkyl magnesium halide with 1 to 6 carbon atoms comprising methyl magnesium bromide (CH3MgBr), ethyl magnesium bromide (CH3CH2MgBr), methyl magnesium chloride (CH3MgCl), ethyl magnesium chloride (CH3CH2MgCl), and the like may be used.

In one example, in the step of preparing the modified initiator, the polar additive may comprise one or more selected from tetrahydrofuran, ditetrahydrofuryl propane, diethyl ether, cycloamyl ether, dipropyl ether, ethylenedimethyl ether, ethylenedimethyl ether, diethylene glycol, dimethyl ether, tert-butoxyethoxyethane bis(2-dimethylaminoethyl) ether, (dimethylaminoethyl)ethyl ether, dioxane, ethylene glycol dimethyl ether, ethylene glycol dibutyl ether, diethylene glycol dimethyl ether, diethylene glycol dibutyl ether, dimethoxybenzene, 2,2-bis(2-oxolanyl)propane, dipiperidinoethane, pyridine, quinuclidine, trimethylamine, triethylamine, tripropylamine, tetramethylethylenediamine, potassium-tert-butyrate, sodium-tert-butyrate, sodium amylate and triphenylphosphine. Specifically, the polar additive may comprise tetrahydrofuran or tetramethylethylenediamine. By adding the polar additive as above at the time of preparing the modified initiator, it is not necessary to add a polar additive separately upon polymer polymerization, and the polymerization initiator composition prepared according to the present invention has high polarity, so that the hydrophobic SSBR and the hydrophilic silica can be effectively dispersed.

In the step of preparing the modified initiator, the compound represented by Formula 2 and the organometallic compound may be reacted in the form of a solution comprising the compound represented by Formula 2 and an organometallic compound solution by containing each a solvent.

As the solvent, a solvent which does not react with an anion, such as a hydrocarbon compound, can be used, and specifically, one or more selected from linear hydrocarbon compounds such as pentane, hexane, heptane and octane; derivatives thereof having branched chains; cyclic hydrocarbon compounds such as cyclohexane and cycloheptane; aromatic hydrocarbon compounds such as benzene, toluene and xylene; and linear and cyclic ethers such as dimethyl ether, diethyl ether, anisole and tetrahydrofuran can be used. Specifically, cyclohexane, hexane, tetrahydrofuran and diethyl ether, and more specifically, cyclohexane can be used.

In one example, the concentration of the solution containing the compound represented by Formula 2 may be 0.1 to 50 wt %, the concentration of the organometallic compound solution may be 0.1 to 30 wt %, and the balance may be the solvent.

In addition, the molar ratio of the compound represented by Formula 2; and the organometallic compound may be 1:5 to 5:1, and specifically, 1:1 to 1:1.2. If the molar ratio of the organometallic compound is higher or lower than the above range, there may be a problem that formation of side reactants and unreacted materials increases.

In the step of preparing the modified initiator, the temperature at which the compound represented by Formula 2 and the organometallic compound are reacted may be −80 to 100° C., and the reaction time may be 0.001 to 90 minutes. If the reaction temperature is too low, there may be a problem that injection raw materials are frozen, and if the reaction temperature is too high, there may be a problem that the initiator is thermally decomposed. If the reaction time is too short, there may be a problem that the reaction conversion rate is low, and if the reaction time is too long, there may be a problem that formation of side reactants increases.

In one example, the equivalence ratio of the polar additive and the compound represented by Formula 2 may be from 1:1 to 1:4. Specifically, the equivalent ratio of the polar additive and the compound represented by Formula (2) may be 1:1.25 to 1:3 or 1:1.5 to 1:2. When the reaction is carried out at the same rate as the above range, the purity of the polymerization initiator can be increased.

The process for producing a polymerization initiator according to the present invention may further comprise a step of reacting the modified initiator produced and the conjugated diene compound after the step of producing the modified initiator.

In one example, as the conjugated diene compound, one or more of 1,3-butadiene (BD), isoprene (IP), 2,3-dimethyl-1,3-butadiene, 1,3-pentadiene, 3-methyl-1,3-pentadiene, 1,3-heptadiene and 1,3-hexadiene can be used, and specifically, 1,3-butadiene or isoprene can be used. The conjugated diene compound may be reacted in the form of a conjugated diene compound solution including a solvent. As the solvent, any solvent may be used as long as it is ordinarily usable. Specifically, cyclohexane, hexane, tetrahydrofuran, diethyl ether and the like can be used, and more specifically, cyclohexane can be used.

For example, the concentration of the conjugated diene compound solution may be 1 to 100 wt %, and the balance may be a solvent. Specifically, the concentration of the conjugated diene compound solution may be 5 to 90 wt %, or 10 to 80 wt %.

In one example, the molar ratio of a compound represented by Formula 2; and the conjugated diene compound may be 1:1 to 1:100, specifically 1:2 to 1:10. If the molar ratio of the conjugated diene compound is higher than the above range, the viscosity of the solution may increase. If the molar ratio of the compounds represented by Formula (2) is lower than the above range, there may be a problem that the compound not attached with the diene compound increases.

Specifically, the temperature at which the conjugated diene compound is reacted may be 10 to 100° C., and the reaction time may be 1 to 60 minutes. When the reaction temperature is too low, there is a problem that the reaction initiation speed is slow, and when the reaction temperature is too high, the initiator may be thermally decomposed. If the reaction time is too short, there is a problem that the reaction time is insufficient. If the reaction time is too long, there is a problem that unnecessary process cost is incurred in a state where the reaction is completed.

In the method for preparing a polymerization initiator according to the present invention, the reactor is not particularly limited as long as it is a reactor following the above process. In one example, as the reactor, a continuous reactor can be used. Specifically, the continuous reactor comprises a mixer; and a first inflow line and a second inflow line connected to the mixer, wherein the first inflow line may supply the compound represented by Formula 2 (and the polar additive) and the second inflow line may supply the organometallic compound. Also, the mixer comprises a first mixer and a second mixer connected in series, and comprises first and second inflow lines connected in the first mixer; and a third inflow line connected to the second mixer, wherein the third inflow line may supply the conjugated diene compound. More specifically, the first and second mixers may comprise one or more of a static mixer and a microreactor, where the static mixer may be a plate mixer, a Kenics mixer or a Sulzer mixer and the microreactor may comprise a plurality of microchannels repeating branching and joining. At this time, the microreactor is a reactor composed of channels with a size of 10 µm to 10 mm and having mixing characteristics using a hydrodynamic structure. It may comprise a plurality of microchannels repeating branching and merging among theses.

For example, a first inflow line may be provided at one end of the first mixer, and a second inflow line may be provided at a horizontal or vertical direction with respect to the first inflow line. Also, a third inflow line may be connected to the second mixer.

FIG. 5 is a schematic configuration diagram of a continuous reactor that can be used in the method for preparing a polymerization initiator of the present invention, where this device may comprise a primary reaction zone (1), a first static mixer (2), a first inflow line (3), a second inflow line (4), a connecting pipe (5), a secondary reaction zone (6), a second static mixer (7), a third inflow line (8) and an outlet (9).

FIG. 6 is a schematic configuration diagram of a polymerization initiator production apparatus according to another example of the present invention, where the apparatus according to this embodiment may be largely composed of a primary reaction zone (10) and a secondary reaction zone (20). The primary reaction zone (10) may comprise a first microreactor (11) and the secondary reaction zone (20) may comprise a second microreactor (21).

The first microreactor (11) is a type of continuous reactor, which may be equipped with a first inflow line (12), a second inflow line (13) and a plurality of microchannels (14, 15). The first inflow line (12) may be supplied with, for example, the compound represented by Formula 2 (and the polar additive), and the second inflow line (13) may be supplied with, for example, the organometallic compound. Specifically, the compound represented by Formula 2 (and the polar additive); and the organometallic compound may be supplied in fluid, and may be supplied in a vapor or liquid state via a fluid communication. In the case of being supplied in a liquid form, the compound represented by Formula 2 (and the polar additive); and the organometallic compound are each capable of fluid supply in the form of containing a solvent.

The microchannels (14, 15) may be connected to or comprise the first inflow line (12) and the second inflow line (13). At least two microchannels (14, 15) may be provided, and they may form a plurality of branch points (junction points) (16) by repeating branching and joining. Although only two microchannels, that is, the upper microchannel (14) and the lower microchannel (15) are illustrated, three or more microchannels are also possible.

In the drawing, the plurality of microchannels (14, 15) forms a regular pattern by periodically branching while forming a rhombic shape, but the overall shape and branching pattern of the plurality of microchannels (14, 15) are not particularly limited, which may be changed as needed, and for example, may be a circle, an ellipse, a spiral, a polygon, and the like, and may be mixed by a linear section and a curved section or may be irregular patterns.

The repetition number of branching and joining in the microchannels (14, 15) is not particularly limited, which may be, for example, 5 to 1,000 times, preferably 10 to 500 times, and more preferably 50 to 200 times. If the repetition number of branching and joining in the microchannels (14, 15), that is, the number of the branching points (junction points) (16) is too small, the mixing effect may be reduced, and if it is too large, the manufacture may become difficult and the size of the mixer may become large.

The size of the microchannels (14, 15) is not particularly limited, which may be, for example, 10 to 10000 micrometers, preferably 50 to 5000 micrometers, and more preferably 100 to 2000 micrometers. Here, the size of the microchannels (14, 15) may mean a diameter when the microchannels (14, 15) are circular, or an average diameter when the microchannels (14, 15) are not circular. The diameter of the microchannels (14, 15) may be the same or different for each channel.

The first microreactor (11) can be divided and manufactured, and can be completed, for example, by dividing it into a top plate and a bottom plate and manufacturing them, and then bonding two plates. The first inflow line (12), the second inflow line (13) and the microchannels (14, 15) may all be configured so as to be arranged on the same plane, and one or more of the first inflow line (12), the second inflow line (13) and the microchannels (14, 15) may also be configured so as to be arranged on another plane. In addition, the plurality of microchannels (14, 15) may be arranged in a two-dimensional (planar) form, or may also have a three-dimensional arrangement structure such as a spiral. Furthermore, the plurality of microchannels (14, 15) is arranged in a horizontal direction, so that each channel may be located at the same height, and alternatively, it is arranged in a vertical direction, so that each channel may have a different height.

For example, the fluid flow in the microchannel mixer divided into the top plate and the bottom plate will be described as follows. While an A solution (an organometallic compound) injected into the top plate and a B solution injected into the bottom plate (a compound represented by Formula 2 and a polar additive) pass through a first branch point, they may branch after the A solution flows into the upper part and the B solution flows into the lower part. That is, the left side of the top plate A solution and the left side of the bottom plate B solution may be divided into the left flow channel and the right side of the top plate A solution and the right side of the bottom plate B solution may be divided into the right flow channel, so as to have the same amount. After the branching, the streams can be induced so that the left stream flows only into the top plate and the right stream flows only into the bottom plate. Thereafter, the fluid flowing into the top plate and the fluid flowing into the bottom plate meet at a second branch point, and the method of again branching and meeting at the next branch point in the same manner as described above can be repeated. Conceptually, the stream of two layers of A/B can be divided into two parts of A/B and A/B at the branching point and then combined top and bottom to make it into the stream of four layers of A/B/A/B, where if this is repeated, the stream is divided by the nth power of 2, so that the interface between A and B is drastically increased, whereby the mixing effect can be maximized.

The second microreactor (21) may be connected in series with the first microreactor (11) via a connecting pipe (17) and may be equipped with a third inflow line (22), an outlet (26), a plurality of microchannels (23, 24) and a branch point (junction point) (25). A primary reactant of the first microreactor (11) may be injected through the connecting pipe (17), and for example, the conjugate diene compound may be injected into the third inflow line (22) and a secondary reactant may be discharged into the outlet (26). The second microreactor (21) may be configured to be the same as or similar to the first microreactor (11).

FIG. 7 shows a detailed structure of microchannels according to another embodiment of the present invention and a fluid flow in the microchannels, and FIG. 8 shows a separation structure and a combination structure of a lower microchannel and an upper microchannel according to another embodiment of the present invention.

The first microreactor (11) may be configured to comprise a top plate and a bottom plate. An upper microchannel (14) having an open bottom can be formed on the top plate and a lower microchannel (15) having an open top can be formed on the bottom plate, where the upper and lower microchannels (14, 15) may be combined to form a closed flow channel. The flow channel may have a rectangular cross section as in the drawing, and may also be manufactured in a circular shape, an elliptical shape, or other polygonal shapes. The upper and lower microchannels (14, 15) may have the respective inflow lines (12a, 13a) and a common outlet (17a). The inflow lines (12a, 13a) may be connected to the inflow lines (12, 13) and the inflow lines (12a, 13a) themselves may also extend to the outside of the top and bottom plates to form the inflow lines (12, 13). The outlet (17a) may be connected to the connecting pipe (17) and the outlet (17a) itself may also extend to the outside of the top and bottom plates to form the connecting pipe (17).

The upper microchannel (14) may be equipped with a plurality of branch points (16a, 16b) disposed along the center, where it is branched into two branches of the left and right branch channels (14a, 14b) at each of branch points (16a, 16b), provided that each right branch channel (14b) may be extended and then blocked, and each left branch channel (14a) may continue to be extended to the next branch point (16b) while being deflected toward the center.

Thus, the reason why one side of the branch channel is blocked and only the other side is continuously connected is to induce the fluid flow of the multi-layer structure. If one side of the branch channel is not blocked, the two fluids may hardly be mixed or the mixing effect may be insignificant.

Similarly, the lower microchannel (15) may be equipped with a plurality of branch points (16a, 16b) disposed along the center, where it is branched into two branches of the left and right branch channels (15a, 15b) at each of branch points (16a, 16b), provided that each left branch channel (15a) may be extended and then blocked, and each right branch channel (15b) may continue to be extended to the next branch point (16b) while being deflected toward the center.

Referring to FIG. 7, a first solution (indicated in gray) selected from a solution containing a compound represented by Formula 2 (and a polar additive) and a organometallic compound solution may be introduced into the inflow line (12a) of the upper microchannel (14) and a second solution (indicated in black) may be introduced into the inflow line (13a) of the lower microchannel (15).

Thereafter, while the upper and lower microchannels (14, 15) are combined, for example, in the case of Point A, the stream of two layers flows into the upper microchannel (14) as the first solution layer and the lower microchannel (15) as the second solution layer.

When it reaches the first branch point (16a), for example, in the case of Point B, the flow rate may increase while the channel width increases.

Thereafter, while it passes through the first branch point (16a), for example, in the case of Point C, it can be branched into a two-layer stream of the left branch channels (14a, 15a) and a two-layer stream of the right branch channels (14b, 15b). Up to this point, it is possible to maintain a two-layer stream of approximately the same flow rate as Point A at each channel.

Thereafter, while it passes through the point where the respective branch channels (14b, 15b) are blocked, for example, in the case of Point D, the left two-layer stream flows only into the left branch channel (14a) of the upper microchannel (14), since the left branch channel (14a) of the upper microchannel (14) is extended and the left branch channel (15a) of the lower microchannel (15) is blocked. Conversely, the right two-layer stream flows only into the right branch channel (15b) of the lower microchannel (15), since the right branch channel (14b) of the upper fine channel (14) is blocked and the right branch channel (15b) of the lower microchannel (15) is extended. At this time, since the fluid flows only into one microchannel, the flow rate of each channel at Point D is reduced to about half of Point C Then, at the second branch point (16b), for example, in the case of Point E, the left two-layer stream that has flowed only upward and the right two-layer stream that has flowed only downward may be joined at the center to form a four-layer stream (first solution layer/second solution layer/first solution layer/second solution layer).

By repeating the above-described process, a multi-layer stream can be formed with the nth power of 2 at each branch point.

In short, after the blue liquid of the bottom plate and the red liquid of the top plate flow, they may be divided into the left and the right at the branch point, and then the right stream may flow only into the bottom plate to be led to the center and the left stream may flow only into the top plate to be led to the center. That is, since the streams that have been divided up and down and introduced are divided into the left and the right, and then led to the center and again gathered up and down, the two divided streams are combined at the center to become the four-layer stream, and the four divided streams are again divided into two at the next branch point and combined at the center to become the eight-layer stream, and thus, as the branch points are repeated, the result is obtained, in which the stream is divided with the nth power of 2.

In this way, when the fluid stream in the microchannel is branched to the right and left, the two branched streams can be led to the center and combined up and down, and when the fluid stream in the microchannel is branched up and down, the two branched streams can be combined to the left and right.

FIG. 9 is a schematic configuration diagram of a polymerization initiator production apparatus according to another embodiment of the present invention, which is an embodiment adding static mixers (19, 28) to the apparatus of FIG. 6. As the static mixers (19, 28), one or more mixers selected from the group consisting of a plate mixer, a Kenics mixer and a Sulzer mixer can be connected in series.

In FIG. 9, the primary reaction zone (10) may comprise a first microreactor (11) and a first static mixer (19), and the secondary reaction zone (20) may comprise a second microreactor (21) and a second static mixer (28). The microreactors (11, 21) and the static mixers (19, 28) may be each connected in series via the connecting pipes (17, 18, 27).

On the other hand, the manufacturing apparatus according to the present invention may be further equipped with a pressure control means for controlling a pressure inside a continuous reactor, in order that each material injected into the continuous reactor can flow to the first microreactor (11) and the second microreactor (21) in the case of FIG. 6, and to the first microreactor (11), the first static mixer (19), the second microreactor (21) and the second static mixer (28) in the case of FIG. 9, in parallel, and prevent the stream in the reverse direction.

That is, according to another embodiment of the present invention, the continuous process type reactor may be further equipped with a pressure control means for controlling an inner pressure. The compound represented by Formula 2 (and the polar additive), the organometallic compound, and the conjugated diene compound injected into the production apparatus by the pressure control means can be mixed and reacted while flowing in the same direction (downstream direction) at a pressure above normal pressure.

If a polymerization initiator is prepared by the method for preparing a polymerization initiator of the present invention and then directly introduced into the solution-polymerized styrene-butadiene polymer (SSBR) synthesis by on-demand manner synthesis, an amine group such as a compound represented by Formula 2 can be introduced into the front-end of the SSBR by solving the conventional initiator storage stability problem and improving the initiator reactivity.

Moreover, the present invention provides a method for preparing a polymer comprising a step of reacting a polymerization initiator composition comprising a compound represented by Formula 1 below; a resin monomer; and a conjugated diene compound:

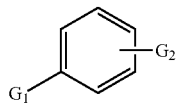

[Formula 1]

In Formula 1 above, $G_1$ and $G_2$ include two or more of ortho, meta and para isomers based on the benzene structure disclosed in Formula 1, but include the case where $G_1$ and $G_2$ are a para isomer, where $G_1$ is a substituent group containing an alkali metal or an alkali earth metal, $G_1$ is a form in which alkyl lithium having 1 to 20 carbon atoms, alkyl sodium having 1 to 20 carbon atoms, alkyl potassium having 1 to 20 carbon atoms, alkyl magnesium bromide having 1 to 6 carbon atoms or alkyl magnesium chloride having 1 to 6 carbon atoms is substituted for the benzene structure disclosed in Formula 1, a polar substituent group forms a coordination bond on the basis of the alkali metal or alkali earth metal contained in $G_1$, and $G_2$ is represented by Formula 1-a below,

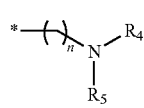

[Formula 1-a]

in Formula 1-a above, $R_4$ and $R_5$ independently represent hydrogen or an alkyl group having 1 to 5 carbon atoms, n is an integer of 0 to 20, the case where n is 0 represents a single bond, in the benzene structure of Formula 1, the carbons to which $G_1$ and $G_2$ are not bonded are independently bonded by hydrogen or an alkyl group having 1 to 6 carbon atoms.

For example, in Formula 1-a, n may be an integer of 0 to 15, an integer of 0 to 10, or an integer of 0 to 5.

In one example, the compound represented by Formula 1 may have a ratio of the sum weight of the ortho and meta isomers to the weight of the para isomer in a range of 1 to 4:6 to 9. Specifically, the ratio of the sum weight of the ortho and meta isomers to the weight of the para isomer may be in a range of 2 to 3:7 to 9. By having the weight ratio of isomers in the above range, the stability of the polymerization initiator composition can be improved.

In addition, in the present invention, when the polymer is prepared using the compound represented by Formula 1, the compound represented by Formula (1) contains a polar substituent group, and thus there is an advantage that the hydrophilic silica particles and the hydrophobic polymer (SSBR) can be effectively dispersed.

In one example, as the type of the resin monomer, one or more selected from the group consisting of styrene and 1,3-butadiene are mainly used, without being limited thereto, which may be applied to all monomers capable of anion initiation.

Specifically, the molar ratio of the compound represented by Formula (1); and the resin monomer may be 1:10 to 1:100,000, specifically 1:100 to 1:50,000. However, it is not limited thereto and can be used in various ratios depending on the SSBR product.

In one example, as the conjugated diene compound, one or more of 1,3-butadiene (BD), isoprene (IP), 2,3-dimethyl-1,3-butadiene, 1,3-pentadiene, 3-methyl-1,3-pentadiene, 1,3-heptadiene and 1,3-hexadiene may be used, and specifically, 1,3-butadiene or isoprene may be used. The conjugated diene compound may be reacted in the form of a conjugated diene compound solution including a solvent. As the solvent, any solvent may be used as long as it is ordinarily usable, and specifically, cyclohexane, hexane, tetrahydrofuran, diethyl ether and the like can be used, and more specifically, cyclohexane can be used.

Specifically, the concentration of the conjugated diene compound solution may be 1 to 100 wt %, and the balance may be the solvent.

Also, the molar ratio of the compound represented by Formula 1; and the conjugated diene compound may be 1:1 to 1:100, and specifically 1:2 to 1:50. If the molar ratio of the conjugated diene compound is higher than the above range, there may be a problem that the viscosity of the solution increases, and if the molar ratio of the compound represented by Formula 1 is lower than the above range, there may be a problem that the compound attached with no diene compound increases.

MODE FOR INVENTION

Hereinafter, the present invention will be described in more detail based on examples, but the following examples are for illustrating the present invention, and the right scope of the present invention is not limited to the following examples.

Preparation Example 1

Two vacuum-dried stainless steel pressure vessels were prepared. 2477 g of hexane, 15 g of 2-vinyl-N,N-dimethylbenzylamine, 5 g of 3-vinyl-N,N-dimethylbenzylamine, 80 g of 4-vinyl-N,N-dimethylbenzylamine and 72 g of tetramethylethylenediamine were placed in the first pressure vessel to prepare a vinyl-N,N-dimethylbenzylamine solution. Then, 171 g of 2.5 M liquid n-butyl lithium and 2478 g of hexane were placed in the other pressure vessel to prepare an n-butyl lithium solution.

The pressure of each pressure vessel was maintained at 4 bar. Then, the vinyl-N,N-dimethylbenzylamine solution was injected into the first inflow line at 10.0 g/min and the n-butyl lithium solution was injected into the second inflow line at 10.0 g/min, using a mass flowmeter, where each stream meets on a T-union or Y-shaped channel. At this time, the width of the tube or channel was ⅛ inch, the temperature was kept at −30° C., and the inner pressure was maintained at 2 bar by using a back pressure regulator. After the two raw materials were mixed, a polymerization initiator composition was prepared by controlling the residence time to be within 5 minutes.

Preparation Example 2

A polymerization initiator composition was prepared in the same manner as in Preparation Example 1, except that 2495 g of hexane and 54 g of tetramethylethylenediamine were added to the first pressure vessel.

Preparation Example 3

A polymerization initiator composition was prepared in the same manner as in Preparation Example 1, except that 2513 g of hexane and 36 g of tetramethylethylenediamine were added to the first pressure vessel.

Preparation Example 4

A polymerization initiator composition was prepared in the same manner as in Preparation Example 1, except that 2531 g of hexane and 18 g of tetramethylethylenediamine were added to the first pressure vessel.

Preparation Example 5

Two vacuum-dried stainless steel pressure vessels were prepared. 2540.4 g of hexane, 108.6 g of N,N-diethyl-4-vinylaniline and 72 g of tetramethylethylenediamine were placed in the first pressure vessel to prepare a solution. Then, 171 g of 2.5 M liquid n-butyl lithium and 2478 g of hexane were placed in the other pressure vessel to prepare an n-butyl lithium solution, and other injection procedures were subjected to the same manner as in Preparation Example 1 to prepare a polymerization initiator composition.

Preparation Example 6

Two vacuum-dried stainless steel pressure vessels were prepared. 2540.3 g of hexane, 108.7 g of N,N-dimethyl-2-(4-vinylphenyl)ethane-1-amine and 72 g of tetramethylethylenediamine were placed in the first pressure vessel to prepare a solution. Then, 171 g of 2.5 M liquid n-butyl lithium and 2478 g of hexane were placed in the other pressure vessel to prepare an n-butyl lithium solution, and other injection procedures were subjected to the same manner as in Preparation Example 1 to prepare a polymerization initiator composition.

Preparation Example 7

Two vacuum-dried stainless steel pressure vessels were prepared. 2531.6 g of hexane, 117.4 g of N,N-diethyl-2-(4-vinylbenzyl)ethane-1-amine and 72 g of tetramethylethylenediamine were placed in the first pressure vessel to prepare a solution. Then, 171 g of 2.5 M liquid n-butyl lithium and 2478 g of hexane were placed in the other pressure vessel to prepare an n-butyl lithium solution, and other injection procedures were subjected to the same manner as in Preparation Example 1 to prepare a polymerization initiator composition.

Preparation Example 8

Two vacuum-dried stainless steel pressure vessels were prepared. 2477 g of hexane, 5 g of N,N-diethyl-2-vinylaniline, 8.6 g of N,N-diethyl-3-vinylaniline and 95 g of N,N-diethyl-4-vinylaniline and 72 g of tetramethylethylenediamine were placed in the first pressure vessel to prepare a solution. Then, 171 g of 2.5 M liquid n-butyl lithium and 2478 g of hexane were placed in the other pressure vessel to prepare an n-butyl lithium solution, and other injection procedures were subjected to the same manner as in Preparation Example 1 to prepare a polymerization initiator composition.

Preparation Example 9

Two vacuum-dried stainless steel pressure vessels were prepared. 2477 g of hexane, 10 g of N,N-dimethyl-2-(2-vinylphenyl)ethane-1-amine, 8.7 g of N,N-dimethyl-2-(3-vinylphenyl)ethane-1-amine, 90 g of N,N-dimethyl-2-(4-vinylphenyl)ethan-1-amine and 72 g of tetramethylethylenediamine were placed in the first pressure vessel to prepare a solution. Then, 171 g of 2.5 M liquid n-butyl lithium and 2478 g of hexane were placed in the other pressure vessel to prepare an n-butyl lithium solution, and other injection procedures were subjected to the same manner as in Preparation Example 1 to prepare a polymerization initiator composition.

Preparation Example 10

Two vacuum-dried stainless steel pressure vessels were prepared. 2477 g of hexane, g of N,N-diethyl-2-(2-vinylphenyl)ethan-1-amine, 16 g of N,N-diethyl-2-(3-vinylphenyl)ethan-1-amine and 100 g of N,N-diethyl-2-(4-vinylphenyl)ethane-1-amine and 72 g of tetramethylethylenediamine were placed in the first pressure vessel to prepare a solution. Then, 171 g of 2.5 M liquid n-butyl lithium and 2478 g of hexane were placed in the other pressure vessel to prepare an n-butyl lithium solution, and other injection procedures were subjected to the same manner as in Preparation Example 1 to prepare a polymerization initiator composition.

Example 1

88.1 g of n-hexane, 3.2 g of styrene as a monomer and 8.7 g of butadiene were mixed with 0.5 g of the polymerization initiator composition of Preparation Example 1 and the mixture was polymerized at 60° C. for 30 minutes.

Example 2

88.1 g of n-hexane, 3.2 g of styrene as a monomer and 8.7 g of butadiene were mixed with 0.5 g of the polymerization initiator composition of Preparation Example 5 and the mixture was polymerized at 60° C. for 30 minutes.

Example 3

88.1 g of n-hexane, 3.2 g of styrene as a monomer and 8.7 g of butadiene were mixed with 0.5 g of the polymerization initiator composition of Preparation Example 6 and the mixture was polymerized at 60° C. for 30 minutes.

Example 4

88.1 g of n-hexane, 3.2 g of styrene as a monomer and 8.7 g of butadiene were mixed with 0.5 g of the polymerization initiator composition of Preparation Example 7 and the mixture was polymerized at 60° C. for 30 minutes.

Example 5

88.1 g of normal hexane, 3.2 g of styrene as a monomer and 8.7 g of butadiene were mixed with 0.5 g of the polymerization initiator composition of Preparation Example 8 and the mixture was polymerized at 60° C. for 30 minutes.

Example 6

88.1 g of n-hexane, 3.2 g of styrene as a monomer and 8.7 g of butadiene were mixed with 0.5 g of the polymerization initiator composition of Preparation Example 9 and the mixture was polymerized at 60° C. for 30 minutes.

Example 7

88.1 g of n-hexane, 3.2 g of styrene as a monomer and 8.7 g of butadiene were mixed with 0.5 g of the polymerization initiator composition of Preparation Example 10 and the mixture was polymerized at 60° C. for 30 minutes.

Comparative Example 1

The polymerization was performed in the same manner as in Example 1, except that n-butyl lithium was used as a polymerization initiator and 1.7 mg of tetramethylethylenediamine was added.

Experimental Example 1

In order to investigate the composition ratios of the polymerization initiator compositions according to the present invention, the liquid chromatography analysis was conducted for Preparation Example 1, and the gas chromatography analysis was conducted for Preparation Examples 1 to 4, and the results were shown in the following FIG. 1 and Tables in FIG. 1.

Referring to FIG. 1, a peak of tetramethylethylenediamine (TEMED) can be confirmed at about 6 minutes, and 3 peaks of materials (products) obtained by reacting 2-vinyl-N,N-dimethylbenzylamine, 3-vinyl-N,N-dimethylbenzylamine and 4-vinyl-N,N-dimethylbenzylamine with butyl lithium, respectively appear at about 19 minutes. Specifically, materials (products) of an ortho form (o-) from 2-vinyl-N,N-dimethylbenzylamine, a meta form (m-) from 3-vinyl-N,N-dimethylbenzylamine and a para form (p-) from 4-vinyl-N,N-dimethylbenzylamine are produced. In addition, it can be confirmed that B1, which is one of by-products, appears at about 29 minutes and B2 appears at about 30 minutes.

Referring to GC Area % values in FIG. 1, it can be seen that as the TEMED equivalent increases, the ratio of the products (sum of o-, m- and p-areas) increases and the ratio of by-products (sum of B1 and B2 areas) decreases.

From these results, it can be seen that when the polar additive (for example, tetramethylethylenediamine) in the polymerization initiator composition according to the present invention has a content of 0.25 equivalents or more relative to one equivalent of the compound represented by Formula 2 (for example, an isomer of vinyl-N,N-dimethylbenzylamine (DMVBA)), the yield of the initiator in the polymerization initiator composition increases.

Experimental Example 2

In order to evaluate the polarity of the polymer composition (polymer) produced by using the polymerization initiator composition according to the present invention, the contact angle test was performed on the polymer compositions prepared in Examples 1 to 7 and Comparative Example 1, and the results were shown in Table 1 below.

TABLE 1

| Sample | $H_2O$ (°) | EG (°) | Formamide (°) | $r^s$ | $r^{sd}$ | $r^{sp}$ | Polarity |
|---|---|---|---|---|---|---|---|
| Example 1 | 91.0 | 67.8 | 78.9 | 21.9 | 16.1 | 5.8 | 0.264 |
| Example 2 | 91.2 | 67.9 | 78.2 | 22.9 | 17.8 | 5.1 | 0.223 |
| Example 3 | 90.6 | 62.0 | 78.0 | 25.1 | 20.0 | 5.1 | 0.203 |
| Example 4 | 90.4 | 62.0 | 77.5 | 28.6 | 23.6 | 5.0 | 0.175 |
| Example 5 | 90.8 | 63.5 | 77.5 | 25.5 | 20.1 | 5.355 | 0.210 |
| Example 6 | 90.2 | 62.1 | 77.5 | 24.0 | 19.5 | 4.536 | 0.189 |
| Example 7 | 91.1 | 65.0 | 78.1 | 25.1 | 20.1 | 4.995 | 0.199 |
| Comparative Example 1 | 90.4 | 58.4 | 76.3 | 26.2 | 22.1 | 4.1 | 0.157 |

Referring to Table 1, it can be confirmed that the polymers prepared in Examples 1 to 7 have larger contact angles with respect to distilled water, ethylene glycol and formamide than the polymer prepared in Comparative Example 1, and the polarity is also 1.7 times higher. In particular, it could be seen that in Example 1, the polarity was 1.7 times higher than that in Comparative Example 1, and in Example 5, the polarity was increased by about 34% as compared with Comparative Example 1. Accordingly, it can be seen that the polymer produced by using the polymerization initiator composition containing isomers in a certain weight ratio in the present invention exhibits excellent physical properties.

From these results, the polymer prepared by the polymerization initiator composition according to the present invention has higher polarity than the polymer prepared by using n-butyl lithium generally used as an initiator, so that the affinity for the silica filler is increased. Therefore, it can be seen that it is advantageous to prepare SSBR having higher fuel efficiency than a general polymer.

Experimental Example 3

In order to examine rheological properties of the polymerization initiator composition according to the present invention, the viscosity, storage elastic modulus (G') and loss elastic modulus (G") were measured on the polymer composition (SSBR solution) of Example 1, and the results were shown in FIGS. 2 to 4 below.

FIG. 2 is a graph of shear viscosity versus shear rate of the polymer prepared in Example 1. Referring to FIG. 2, the polymerization composition of Example 1; the composition obtained by mixing 15% of silica with the polymer composition of Example 1; and the composition obtained by mixing 30% of silica with the polymer composition of Example 1 were experimented, and it can be seen that the more the silica particles are added to the polymer composition prepared in Example 1, the more the viscosity is improved.

Furthermore, FIG. 3 is a graph of storage elastic modulus and loss elastic modulus versus pressure (strain) of the polymer composition prepared in Example 1. Referring to FIG. 3, the polymerization composition of Example 1; the composition obtained by mixing 15% of silica with the polymer composition of Example 1; and the composition obtained by mixing 30% of silica with the polymer composition of Example 1 were experimented, and it can be seen that as the content of the silica particles added to the polymer composition of Example 1 increases, the storage elastic modulus and the loss elastic modulus are greatly improved.

In addition, FIG. 4 is a graph of storage elastic modulus and loss elastic modulus versus frequency of the polymer composition prepared in Example 1. Referring to FIG. 4, the polymerization composition of Example 1; the composition obtained by mixing 15% of silica with the polymer composition of Example 1; and the composition obtained by mixing 30% of silica with the polymer composition of Example 1 were experimented, and it can be seen that the storage elastic modulus and the loss elastic modulus of each composition do not only increase as the frequency increases, but also the storage elastic modulus and the loss elastic modulus are greatly improved as the content of the silica particles added to the polymer composition of Example 1 increases.

Through these results, it can be seen that the polymer composition according to the present invention disperses the polymer particles well, because the viscosity and the elasticity are both increased when the silica particles have been dispersed in the polymer composition prepared in Example 1.

INDUSTRIAL APPLICABILITY

By the polymerization initiator composition in which isomers of the polymerization initiator are mixed, the present invention can prevent instability and inertness of the polymerization initiator and physical property degradation of the SSBR, minimize by-products and unreacted materials, and remarkably improve a conversion ratio, thereby reducing the manufacturing process time and improving the manufacturing process efficiency.

The invention claimed is:

1. A polymerization initiator composition comprising a compound represented by Formula 1 below:

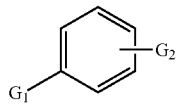

[Formula 1]

wherein,
$G_1$ and $G_2$ include two or more of ortho, meta or para isomers based on a benzene structure of the compound represented by Formula 1, and
include the case when $G_1$ and $G_2$ are a para isomer,
wherein $G_1$ is a substituent group containing an alkali metal or an alkali earth metal,
$G_1$ is a form in which alkyl lithium having 1 to 20 carbon atoms, alkyl sodium having 1 to 20 carbon atoms, alkyl potassium having 1 to 20 carbon atoms, alkyl magnesium bromide having 1 to 6 carbon atoms or alkyl magnesium chloride having 1 to 6 carbon atoms is substituted for the benzene structure disclosed in Formula 1,
a polar substituent group forms a coordination bond on the basis of the alkali metal or alkali earth metal contained in $G_1$, and
$G_2$ is represented by Formula 1-a below,

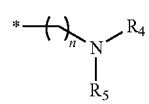

[Formula 1-a]

wherein,
$R_4$ and $R_5$ independently represent hydrogen or an alkyl group having 1 to 5 carbon atoms,
n is an integer of 0 to 2,
wherein n equals 0 represents a single bond, and
in the benzene structure of the compound represented by Formula 1, carbons to which $G_1$ and $G_2$ are not bonded are independently bonded by hydrogen or an alkyl group having 1 to 6 carbon atoms.

2. The polymerization initiator composition according to claim 1,
wherein the compound represented by Formula 1 has a ratio of the sum weight of the ortho and meta isomers to the weight of the para isomer in a range of 1 to 4:6 to 9.

3. The polymerization initiator composition according to claim 1,
wherein the polar substituent group has a structure in which one or more selected from the group consisting of tetrahydrofuran, ditetrahydrofurylpropane, diethyl ether, cycloamyl ether, dipropyl ether, ethylenedimethyl ether, ethylenedimethyl ether, diethylene glycol, dimethyl ether, tert-butoxyethoxyethane, bis(2-dimethylaminoethyl) ether, (dimethylaminoethyl)ethyl ether, dioxane, ethylene glycol dimethyl ether, ethylene glycol dibutyl ether, diethylene glycol dimethyl ether, diethylene glycol dibutyl ether, dimethoxybenzene, 2,2-bis(2-oxolanyl)propane, dipiperidinoethane, pyridine, quinuclidine, trimethylamine, triethylamine, tripropylamine, tetramethylethylenediamine, potassium tert-butyrate, sodium tert-butyrate, sodium amylate or and triphenylphosphine are coordination-bonded to the alkali metal or the alkali earth metal contained in $G1$.

4. A method for preparing a polymerization initiator composition according to claim 1 comprising:
reacting a compound represented by Formula 2 below and an organometallic compound to prepare a modified initiator; and
reacting the modified initiator and a polar additive:

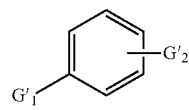

[Formula 2]

wherein,
$G'_1$ and $G'_2$ include two or more of ortho, meta or para isomers based on a benzene structure of the compound represented by Formula 2, and
include the case where $G'_1$ and $G'_2$ are a para isomer,
where $G'_1$ is represented by Formula 2-a below and
$G'_2$ is represented by Formula 2-b below,

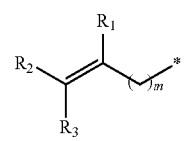

[Formula 2-a]

wherein, $R_1$, $R_2$ and $R_3$ independently represent hydrogen, an alkyl group having 1 to 6 carbon atoms, an alkenyl group having 1 to 6 carbon atoms or an alkynyl group having 1 to 6 carbon atoms, m is an integer of 0 to 20, and wherein m equals 0 represents a single bond, and

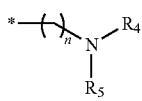

[Formula 2-b]

wherein, $R_4$ and $R_5$ independently represent hydrogen or an alkyl group having 1 to 5 carbon atoms, n is an integer of 0 to 2, wherein n equals 0 represents a single bond, and in the benzene structure of the compound represented by Formula 2, carbons to which $G'_1$ and $G'_2$ are not bonded are independently bonded by hydrogen or an alkyl group having 1 to 6 carbon atoms.

5. The method for preparing a polymerization initiator composition according to claim 4, wherein the compound represented by Formula 2 has a ratio of the sum weight of the ortho and meta isomers to the weight of the para isomer in a range of 1 to 4:6 to 9.

6. The method for preparing a polymerization initiator composition according to claim 4, wherein the organometallic compound comprises an organic alkali metal compound or an organic alkali earth metal compound.

7. The method for preparing a polymerization initiator composition according to claim 4, wherein a molar ratio of the compound represented by Formula 2 to the organometallic compound is 5:1 to 1:5.

8. The method for preparing a polymerization initiator composition according to claim 4, wherein the polar additive comprises one or more selected from the group consisting of tetrahydrofuran, ditetrahydrofurylpropane, diethyl ether, cycloamyl ether, dipropyl ether, ethylenedimethyl ether, ethylenediethyl ether, diethylene glycol, dimethyl ether, tert-butoxyethoxyethane, bis(2-dimethylaminoethyl) ether, (dimethylaminoethyl)ethyl ether, dioxane, ethylene glycol dimethyl ether, ethylene glycol dibutyl ether, diethylene glycol dimethyl ether, diethylene glycol dibutyl ether, dimethoxybenzene, 2,2-bis(2-oxolanyl) propane, dipiperidinoethane, pyridine, quinuclidine, trimethylamine, triethylamine, tripropylamine, tetramethylethylenediamine, potassium tert-butyrate, sodium tert-butyrate, sodium amylate and triphenylphosphine.

9. The method for preparing a polymerization initiator composition according to claim 4, wherein an equivalent ratio of the polar additive to the compound represented by Formula 2 is 1:1 to 1:4.

10. A method for preparing a polymer comprising:

reacting a polymerization initiator composition comprising a compound represented by Formula 1 according to claim 1; a resin monomer; and a conjugated diene compound:

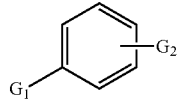

[Formula 1]

wherein, $G_1$ and $G_2$ include two or more of ortho, meta or para isomers based on the benzene structure disclosed in Formula 1, and include the case when $G_1$ and $G_2$ are a para isomer, where $G_1$ is a substituent group containing an alkali metal or an alkali earth metal, $G_1$ is a form in which alkyl lithium having 1 to 20 carbon atoms, alkyl sodium having 1 to 20 carbon atoms, alkyl potassium having 1 to 20 carbon atoms, alkyl magnesium bromide having 1 to 6 carbon atoms or alkyl magnesium chloride having 1 to 6 carbon atoms is substituted for the benzene structure of the compound represented by Formula 1, a polar substituent group forms a coordination bond on the basis of the alkali metal or alkali earth metal contained in $G_1$, and $G_2$ is represented by Formula 1-a below,

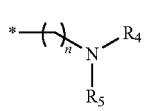

[Formula 1-a]

wherein, $R_4$ and $R_5$ independently represent hydrogen or an alkyl group having 1 to 5 carbon atoms, n is an integer of 0 to 2, wherein n equals 0 represents a single bond, and in the benzene structure of the compound represented by Formula 1, carbons to which $G_1$ and $G_2$ are not bonded are independently bonded by hydrogen or an alkyl group having 1 to 6 carbon atoms.

11. The method for preparing a polymer according to claim 10, wherein the resin monomer is styrene or 1,3-butadiene.

12. The method for preparing a polymer according to claim 10, wherein a molar ratio of the polymerization initiator composition comprising the compound represented by Formula 1 to the conjugated diene compound is 1:1 to 1:100.

* * * * *